(12) United States Patent
Knutson et al.

(10) Patent No.: US 6,903,083 B2
(45) Date of Patent: Jun. 7, 2005

(54) STABILIZED HYDROXYVITAMIN D (75) Inventors: Joyce C. Knutson, Madison, WI (US); Richard B. Mazess, Madison, WI (US); Charles W. Bishop, Mount Horeb, WI (US)

(73) Assignee: Bone Care International, Inc., Middleton, WI (US)

( * ) Notice: Subject to any disclaimer, the term of this patent is extended or adjusted under 35 U.S.C. 154(b) by 0 days.

(21) Appl. No.: 10/223,986

(22) Filed: Aug. 20, 2002

(65) Prior Publication Data

US 2003/0045509 A1 Mar. 6, 2003

Related U.S. Application Data (63) Continuation-in-part of application No. PCT/US01/22729, filed on Jul. 18, 2001.
(60) Provisional application No. 60/219,068, filed on Jul. 18, 2000.

(51) Int. Cl.⁷ .................... A61K 31/592; C07C 401/00
(52) U.S. Cl. ........................................ 514/167; 552/653
(58) Field of Search ........................... 552/653; 514/167

(56) References Cited

U.S. PATENT DOCUMENTS

| | | |
|---|---|---|
| 2,383,446 A | 6/1945 | Calcott et al. |
| 3,697,559 A | 10/1972 | DeLuca et al. |
| 3,741,996 A | 6/1973 | DeLuca et al. |
| 3,907,843 A | 9/1975 | DeLuca et al. |
| 4,160,803 A | 7/1979 | Potts |
| 4,195,027 A | 3/1980 | DeLuca et al. |
| 4,202,829 A | 5/1980 | DeLuca et al. |
| 4,225,596 A | 9/1980 | DeLuca |
| 4,234,495 A | 11/1980 | DeLuca et al. |
| 4,248,867 A | 2/1981 | Ikushima et al. |
| 4,260,549 A | 4/1981 | DeLuca et al. |
| 4,362,710 A | 12/1982 | Watanabe |
| 4,391,802 A | 7/1983 | Suda et al. |
| 4,508,651 A | 4/1985 | Baggiolini et al. |
| 4,554,106 A * | 11/1985 | DeLuca et al. ............. 552/653 |
| 4,555,364 A | 11/1985 | DeLuca et al. |
| 4,588,716 A | 5/1986 | DeLuca et al. |
| 4,661,294 A | 4/1987 | Holick et al. |
| 4,689,180 A | 8/1987 | DeLuca et al. |
| 4,698,328 A | 10/1987 | Neer et al. |
| 4,717,721 A | 1/1988 | DeLuca et al. |
| 4,728,643 A | 3/1988 | Holick et al. |
| 4,833,125 A | 5/1989 | Neer et al. |
| 4,866,048 A | 9/1989 | Calverley et al. |
| 4,902,481 A | 2/1990 | Clark et al. |
| 4,948,789 A | 8/1990 | Slatopolsky |
| 5,037,816 A | 8/1991 | Holick et al. |
| 5,063,221 A | 11/1991 | Nishii et al. |
| 5,087,619 A | 2/1992 | Baggiolini et al. |
| 5,098,899 A | 3/1992 | Gilbert et al. |
| 5,104,864 A | 4/1992 | DeLuca et al. |
| 5,141,719 A | 8/1992 | Fernwood et al. |
| 5,145,846 A | 9/1992 | Baggiolini et al. |
| 5,157,135 A | 10/1992 | Tsuji et al. |
| 5,194,248 A | 3/1993 | Holick |
| 5,205,989 A | 4/1993 | Aysta |
| 5,219,528 A | 6/1993 | Clark |
| 5,232,836 A | 8/1993 | Bouillon et al. |
| 5,260,290 A | 11/1993 | DeLuca et al. |
| 5,264,184 A | 11/1993 | Aysta et al. |
| 5,264,618 A | 11/1993 | Felgner et al. |
| 5,321,018 A | 6/1994 | DeLuca |
| 5,334,740 A | 8/1994 | Takahashi et al. |
| 5,338,532 A | 8/1994 | Tomalia et al. |
| 5,366,965 A | 11/1994 | Strein |
| 5,372,996 A | 12/1994 | Labrie |
| 5,403,831 A | 4/1995 | DeLuca et al. |
| 5,417,923 A | 5/1995 | Bojanic et al. |
| 5,472,957 A * | 12/1995 | Hesse et al. ................. 514/167 |
| 5,478,816 A | 12/1995 | Shah |
| 5,487,900 A | 1/1996 | Itoh et al. |
| 5,488,120 A | 1/1996 | Knutson et al. |
| 5,512,554 A | 4/1996 | Baggiolini et al. |
| 5,527,524 A | 6/1996 | Tomalia et al. |

(Continued)

FOREIGN PATENT DOCUMENTS

| | | |
|---|---|---|
| EP | 0197514 | 10/1986 |
| EP | 0390097 | 10/1990 |
| EP | 0503630 | 9/1992 |
| EP | 0508756 | 10/1992 |
| EP | 0562497 | 9/1993 |
| EP | 0664287 | 7/1995 |
| WO | WO 84/04527 | 11/1984 |
| WO | WO 87/00834 | 2/1987 |
| WO | WO 90/10620 | 9/1990 |
| WO | WO 92/05130 | 4/1992 |
| WO | WO 92/12165 | 7/1992 |
| WO | WO 92/21355 | 12/1992 |
| WO | WO 93/07883 | 4/1993 |
| WO | WO 93/14763 | 8/1993 |
| WO | WO 94/16711 | 8/1994 |
| WO | 96/02501 | 2/1996 |
| WO | WO 96/40153 | 12/1996 |
| WO | WO 99/49870 | 10/1999 |
| WO | 00/43361 | 7/2000 |
| WO | 01/02352 A1 | 1/2001 |

OTHER PUBLICATIONS

H.E. Parren et al., *J. Org. Chem.*, vol. 45, No. 16, 1980, pp. 3253–3258.

Aloia, J. et al., "Calcitriol in the Treatment of Postmenopausal Osteoporosis," *Amer. J. Med.*, (1988) 84:401–08.

(Continued)

Primary Examiner—Barbara P. Badio
(74) Attorney, Agent, or Firm—Teresa J. Welch; Jeffrey D. Peterson; Michael Best & Friedrich LLP (57) ABSTRACT

The invention provides a stabilized 1α-hydroxyvitamin D ("SHVD") which is particularly well suited for pharmaceutical formulations.

19 Claims, 2 Drawing Sheets

U.S. PATENT DOCUMENTS

| | | |
|---|---|---|
| 5,529,991 A | 6/1996 | Knutson et al. |
| 5,554,386 A | 9/1996 | Groman et al. |
| 5,561,123 A | 10/1996 | DeLuca et al. |
| 5,597,575 A | 1/1997 | Breitbarth |
| 5,602,116 A | 2/1997 | Knutson et al. |
| 5,612,327 A | 3/1997 | Makino et al. |
| 5,614,513 A | 3/1997 | Knutson et al. |
| 5,637,742 A | 6/1997 | Valles et al. |
| 5,661,025 A | 8/1997 | Szoka, Jr. et al. |
| 5,663,157 A | 9/1997 | Steinmeyer et al. |
| 5,665,716 A | 9/1997 | Kirsch et al. |
| 5,691,328 A | 11/1997 | Peterson et al. |
| 5,739,271 A | 4/1998 | Sridhar et al. |
| 5,753,638 A | 5/1998 | Baggiolini et al. |
| 5,763,428 A | 6/1998 | Knutson et al. |
| 5,789,399 A | 8/1998 | Strube |
| 5,795,882 A | 8/1998 | Bishop et al. |
| 5,834,016 A | 11/1998 | Naeff et al. |
| 5,902,806 A | 5/1999 | Ikeda et al. |
| 5,905,074 A | 5/1999 | Schneider |
| 5,952,317 A | 9/1999 | Deluca et al. |
| 5,962,731 A | 10/1999 | Boehm et al. |
| 5,972,917 A | 10/1999 | Bishop et al. |
| 5,976,784 A | 11/1999 | DeLuca et al. |
| 6,087,350 A | 7/2000 | Johnson et al. |
| 6,103,709 A | 8/2000 | Norman et al. |
| 6,143,910 A | 11/2000 | Bishop et al. |
| 6,147,064 A | 11/2000 | Knutson et al. |
| 6,211,168 B1 | 4/2001 | Bishop et al. |
| 6,218,430 B1 | 4/2001 | Allegretto et al. |
| 6,221,911 B1 | 4/2001 | Lavin et al. |
| 6,242,434 B1 | 6/2001 | Bishop et al. |
| 6,242,435 B1 | 6/2001 | Achkar |
| 6,251,883 B1 | 6/2001 | Horst et al. |
| 6,329,357 B1 | 12/2001 | Norman et al. |
| 6,369,098 B1 | 4/2002 | Pershadsingh et al. |
| 6,369,099 B1 | 4/2002 | DeLuca et al. |
| 6,395,784 B1 | 5/2002 | Ryono |
| 6,432,936 B1 * | 8/2002 | DeLuca et al. ............. 514/167 |
| 6,432,962 B2 | 8/2002 | Horneman |
| 6,458,827 B2 | 10/2002 | DeLuca et al. |
| 6,482,812 B2 | 11/2002 | DeLuca et al. |
| 6,506,912 B2 | 1/2003 | DeLuca et al. |
| 6,521,222 B1 | 2/2003 | Philippe et al. |
| 6,521,608 B1 | 2/2003 | Henner et al. |
| 6,524,594 B1 | 2/2003 | Santora et al. |
| 6,531,460 B1 | 3/2003 | Takenouchi et al. |
| 6,537,982 B1 | 3/2003 | Bishop et al. |
| 6,541,670 B2 | 4/2003 | Ottosen |
| 6,548,489 B2 | 4/2003 | Takenouchi et al. |
| 6,552,009 B2 | 4/2003 | Achkar |
| 6,555,710 B1 | 4/2003 | Ottosen |
| 6,559,139 B1 | 5/2003 | Johnson et al. |
| 6,566,554 B1 | 5/2003 | Ottosen |
| 6,582,710 B2 | 6/2003 | Deckers et al. |
| 6,599,513 B2 | 7/2003 | Deckers et al. |
| 6,642,218 B2 | 11/2003 | Steinmeyer et al. |
| 2001/0002396 A1 | 5/2001 | Achkar |
| 2001/0025036 A1 | 9/2001 | DeLuca et al. |
| 2001/0049365 A1 | 12/2001 | Achkar |
| 2001/0051617 A1 | 12/2001 | DeLuca et al. |
| 2002/0006917 A1 | 1/2002 | DeLuca et al. |
| 2002/0049344 A1 | 4/2002 | Steinmeyer et al. |
| 2002/0068723 A1 | 6/2002 | DeLuca et al. |
| 2002/0091109 A1 | 7/2002 | Takenouchi et al. |
| 2002/0099039 A1 | 7/2002 | Takenouchi et al. |
| 2002/0103173 A1 | 8/2002 | Takenouchi et al. |
| 2002/0132799 A1 | 9/2002 | Takenouchi et al. |
| 2003/0040508 A1 | 2/2003 | DeLuca et al. |
| 2003/0109506 A1 | 6/2003 | Hayes et al. |
| 2003/0119795 A1 | 6/2003 | Henner et al. |
| 2003/0149005 A1 | 8/2003 | Posner et al. |
| 2003/0149006 A1 | 8/2003 | Steinmeyer et al. |
| 2003/0166622 A1 | 9/2003 | Steinmeyer et al. |
| 2003/0171342 A1 | 9/2003 | Posner et al. |
| 2003/0195171 A1 | 10/2003 | Daifotis et al. |
| 2003/0195176 A1 | 10/2003 | Kawase et al. |
| 2003/0195259 A1 | 10/2003 | Bernardon et al. |
| 2003/0216359 A1 | 11/2003 | Johnson et al. |
| 2004/0019023 A1 | 1/2004 | Morikawa et al. |

OTHER PUBLICATIONS

Barton, D. et al., "Synthetic Uses of Steroidal Ring & Diene Protection: 22,23–Dihydroergosterol," *JCS Perkin I*, (1976) pp. 821–826.

Beer, et al., "A Phase I Trial of Pulse Calcitriol in Patients with Refractory Malignancies," *Cancer*, (Jun. 15, 2001) 91:12:2431–2439.

Beer, et al., "Weekly High–Dose Calcitriol and Docetaxel in Advanced Prostate Cancer," *Seminars in Oncology*, Suppl 15 (Aug. 2001) 28:4:49–55.

Beer, T. et al., "Weekly High–Dose Calcitriol and Docetaxel in Metastatic Androgen–Independent Prostate Cancer," *Journal of Clinical Oncology*, (Jan. 2003) 21:1:123–128.

Blazsek, I. et al. "Combined Differentiation Therapy in Myelodysplastic Syndrome with Retinoid Acid, 1α25 Dihydroxyvitamin $D_3$, and Prednisone," *cancer detection & prevention* 16:4:259–264 (Abstract), 1992.

Brautbar, N. "Osteoporosis: Is 1,25–(OH)2D3 of Value in Treatment?" *Nephron* (1986) 44:161–166.

Braunwald, E. et al., *Harrison's Principles of Internal Medicine*: Part Eleven, "Disorders of Bone and Mineral Metabolism," Chapter 335, McGraw–Hill, New York, (1987) pp. 1860–1865.

Brown, J.P. et al., "Serum Bone Gala–Protein: A Specific Marker for Bone Formation in Postmenopausal Osteoporosis," *Lancet*, (1984) 1:1091–1093.

Caniggia, A. et al., "Effect of a Long–Term Treatment with 1,25–Dihydroxyvitamin $D_3$ on Osteocalcin in Postmenopausal Osteoporosis," *Cacified Tissue Int.*, (1986) 38:328–332.

Christiansen, C. et al., "Prevention of Early Postmenopausal Bone Loss: Controlled 2–Year Study in 315 Normal Females," *Europ J Clin Inves.*, (1980) 10:273–279.

Christiansen, C. et al., "Effect of 1,25–Dihydroxy–Vitamin $D_3$ is Itself or Combined with Hormone Treatment in Preventing Postmenopausal Osteoporosis," *Eur. J. Clin. Invest.*, (1981) 11:305–309.

Crump, D.R. et al., "(22S)–Hydroxyvitamin $D_4$," *J.C.S. Perkins Trans. I*, (1973) pp. 2731–2733.

Cho, Y.L. et al., "Combined Effects of 1,25–Dihydroxyvitamin $D_3$ and Platinum Drugs on the Growth of MCF–7 Cells," *Cancer Research*, (Jun. 1991) 51:2848–2853.

Defacque, H. et al., "Different Combinations of Retinoids and Vitamin $D_3$ Analogs Efficiently Promote Growth Inhibition and Differentiation of Myelomonocytic Leukemia Cell Lines," *J. Pharmacology and Experimental Therapeutics*, (1994)271:193–199.

DeLuca et al., "Synthesis, Biological Activity, and Metabolism of 22,23–$^3$H–Vitamin $D_4$, " *Arch. Biochem, Biophys.*, (1968) 124:122–128.

Duda et al., "1,25–Dihydroxyvitamin D Stimulation Test for Osteoblast Function in Normal and Osteoporotic Postmenopausal Women," *J. Clinic Inves.*, (1987) 79:1249–1253.

Endo, K. et al., "Effect of Combination Treatment with Vitamin D Analog (OCT) and a Bisphosphonate (AHPrBP) in a Nude Mouse Model of Cancer–Associated Hypercalcemia," *Journal of Bone and Mineral Research*, (1998) 13:9:1378–1383.

Foldes, J. et al., "Long Term Treatment with $1\alpha(OH)D_3$ for Postmenopausal Osteoporosis: Efficacy and Safety," *Osteoporosis*, (1987) 2:971–973.

Gallagher, J.C., et al., "Treatment of Postmenopausal Osteoporosis with High Doses of Synthetic Calcitriol," *Annals of Int. Med.*, (1990) 13:649–655.

Gallagher, J.C. et al., "Effects of Increasing Doses of $1\alpha$–Hydroxyvitamin $D_2$ on Calcium Homeostasis in Postmenopausal Osteopenic Women," *J. Bone Min. Res.*, (1994) 9:5:607–614.

Guidelines for the Clinical Evaluation of Drugs Used in the Treatment of Osteoporosis, HEW (FDA) 80– 3094, (1979) pp. 5–6.

Hershberger, P. et al. "Calcitriol (1,25–Dihydroxycholecalciferol) Enhances Paclitaxel Antitumor Activity in Vitro and in Vivo and Accelerates Paclitaxel–induced Apoptosis," *Clinical Cancer Research*, (Apr. 2001) 7:1043–1051.

Hoikka, V. et al., "Treatment of Osteoporosis with 1–Alpha–Hydroxycholecalciferol and Calcium," *Acta. Med. Scand.*(1980) 207:221–224.

Holick, M.F. et al., "Identification of 1,25–Dihydroxycholecalciferol, a Form of Vitamin $D_3$ Metobolically Active in the Intestine," *Proc. Natl. Acad. Sci. USA*, (1971) 68:803–804.

Holick, M.F. et al., "$1\alpha$–Hydroxy Derivative of Vitamin $D_3$: A Highly Potent Analog of $1\alpha 25$ Dihydroxyvitamin $D_3$," *Science* (1973) pp. 180, 190–191.

Holick, M.F., "Noncalcemic Actions of 1,25–Dihydroxyvitamin $D_3$ and Clinical Applications", *Bone*, (1995) 17:2:107S–110S.

Horst et al., "Quantitation of Vitamin D and its Metabolites and Their Plasma Concentrations in Five Species of Animals" *Anal. Biochem.*, (1981) 116:189–203.

Horst et al., "Discrimination in the Metabolism of Orally Dosed Ergocalciferol and Cholecalciferol by the Pig, Rat and Chick," *Biochem. J.*, (1982) 204:185–189.

Jensen, G.F. et al., "Treatment of Post Menopausal Osteoporosis. A Controlled Therapeutic Trial Comparing Oestrogen/Gestagen, 1,25–Dihydroxy–Vitamin $D_3$ and Calcium," *Clin. Endocrinol.*, (1982) 16:515–524.

Johnson, C. et al., "Vitamin D–related Therapies in Prostate Cancer," *Cancer and Metastasis Review* 21, (2002) pp. 147–158.

Jones, G. et al., "Isolation and Identification of 1,25–Dihydroxyvitamin $D_2$," *Biochemistry*, (1975) 14:1250–1256.

Kanis, J.A. et al., "Guidelines for Clinical Trials in Osteoporosis, A Position Paper of the European Foundation for Osteoporosis," *Osteoporosis Int.*, (1991) 1:182–188.

Kim, S. et al., Potentiation of 1,25–Dihydroxyvitamin $D_3$–Induced Differentiation of Human Promyelocytic Leukemia Cells into Monocytes by Costunolide, a Germacranolide Sesquiterpene Lactone, *Biochem. Pharmacology*, (2002) 64:1233–1242.

Knutson, et al., "Metabolism of $1\alpha$–Hydroxyvitamin $D_2$ to activated Dihydroxyvitamin $D_2$ Metabolites Decreases Endogenous $1\alpha 25$–Dihydroxyvitamin $D_3$ in Rats and Monkeys," *Endocrinology*, (1995) 136:11:4749–4753.

Kocienski, P.J. et al., "Calciferol and its Relatives. A Synthesis of Vitamin $D_4$," *J.C.S. Perkins I*, (1979) pp. 1290–1293.

Lam, H.Y. et al., "$1\alpha$–Hydroxyvitamin $D_2$: A Potent Synthetic Analog of Vitamin $D_2$," *Science*, (1974) 486:1038–1040.

Londowski, J.M. et al., "Biological Activity of the C–1, C–3, C–25, β–D–Glucopyranosides of 1,25–Dihydroxyvitamin $D_3^1$," *J. Pharmacology Expr. Ther.*, (1986) 237:3:837–840.

Majewski, et al., "Inhibition of Tumor Cell–Induced Angiogenisis by Retinoids, 1,25–Dihydroxyvitamin $D_3$ and their Combination," *Cancer Letters*, (1993) 75:35–39.

Martin and DeLuca, "Calcium Transport," *Am. J. Physiol.*, 216:1352–1359, 1968.

Mathias, C.J. et al., "Tumor–Selective Radiopharmaceutical Targeting Via Receptor–Mediated Endocytosis of Gallium–67–Deferoxamine–Folate," *J. Nucl. Med.* (1996), 37(6): 1003–1008.

McDonald, F.G., "The Multiple Nature of Vitamin D," *J. Biol. Chem.* 114, (1936) 1xv.

*Merck Index*, S. Budavari (ed.), 11th ed., Merck & Co., Rahway, N.J. (1989) pp. 1579, #9930.

Miller et al., "The Human Prostatic Carcinoma Cell Line LNCaP Expresses Biologically Active, Specific Receptors for $1\alpha,25$–Dihydroxyvitamin $D_3^1$," *Cancer Res.*, (1992) 52:515–520.

Moffatt, K. et al., "$1\alpha,25$–Dihydroxyvitamin $D_3$ and Platinum Drugs Act Synergistically to Inhibit the Growth of Prostate Cancer Cell Lines," *Clinical Cancer Research*, (Mar. 1999) 5:695–703.

Muindi, J. et al., "Pharmacokinetics of High–Dose Oral Calcitriol: Results From a Phase 1 Trial of Calcitriol and Paclitaxel," *Clinical Pharmacology & Therapeutics*, (Dec. 2002) pp. 648–659.

Nemeto, H. et al., "A Stereoselective Synthesis of 1 α–Hydroxy–Vitamin $D_3$," *CHEMISTRY LETTERS*, (1985) 8:1131–1132.

Orimo, H. et al., "Reduced Occurrence of Vertebral Crush Fractures in Senile Osteoporosis Treated with $1\alpha(OH)$–Vitamin $D_3$," *Bone and Mineral*, (1987) 3:47–52.

Ott, S.M. et al., "Calcitriol Treatment is not Effective in Postmenopausal Osteoporosis," *Annals of Int. Med.*, (1989) 110:4:267–274.

Packman, K. et al. "Combination Treatment of MCF–7 Xenografts with the Vitamin $D_3$ Analog EB1089 and Antiestrogens," (Vitamin D Endocrine Workshop, Nashville, TN May 27–Jun. 1, 2000) pp. 511–514.

Podenphant, J. et al., "Serum Bone Gla Protein and Other Biochemical Estimates of Bone Turnover in Early Postmenopausal Women During Prophylactic Treatment for Osteoporosis," *Acta Med Scand*, (1985) 218:329–333.

*Physician's Desk Reference*, Edition 43:1746–1748.

Pouilles, J.M. et al., "Prevention of Early Postmenopausal Bone Loss with 1 α–Hydroxy Vitamin $D_3$, A Three–Year Prospective Study," *Clin Rheumatol.* 11, 4 (1992) pp. 492–497.

Ravid, A. et al., "1,25–Dihydroxyvitamin $D_3$ Enhances the Susceptibility of Brease Cancer Cells to Doxorubicin–induced Oxidative Damage," *Cancer Research*, (Feb. 15, 1999) 59:862–867.

Reeve, L.E. et al., "Biological Activity of $1\alpha$–hydroxy Vitamin $D_2$ in the Rat," *Arch. Biochem. Biophys.* (Feb. 1978) 186:1:164–167.

Sato, F. et al., "Biological Activity of $1\alpha,25$–Dihydroxyvitamin D Derivatives—24–*epi*–$1\alpha,25$–Dihydroxyvitamin D–2 and $1\alpha,25$–Dihydroxyvitamin D–7," *Biochim. Biophys. Acta*, (1991) 1091:188–192.

Shiraki, M. et al., Long–Term Treatment of Postmenopausal Osteoporosis with Active Vitamin $D_3$, 1–Alpha–Hydroxycholecalciferol (1α–$OHD_3$) and 1,24 Dihydroxycholecalciferol (1,24$(OH)_2D_3$), *Endocrinol. Japan*, (1985) 32:305–315.

Siwinska, A. et al. "Potentiation of the Antiproliferative Effect in Vitro of Doxorubicin, Cisplatin and Genistein by New Analogues of Vitamin D," *Anticancer Research*, (2001) 21:1925–1929.

Sjoden et al., "Effects of 1 $OHD_2$ on Bone Tissue," *Acta. Endocrinol*, (Copenh.) (Aug. 1984) 16:4:564–568.

Sjoden, G. et al., "Antirachitic Activity of 1α–Hydroxyergocalciferol and 1α–Hydroxycholecalciferol in Rats," *J. Nutr.*, (1984) 114:2043–2046.

Sjoden, G. et al., "1α–Hydroxyvitamin $D_2$ is Less Toxic than 1α–Hydroxyvitamin $D_3$ in the Rat," *Proc. Soc. Exp. Biol. Med.*, (1985) 178:432–436.

Skowronski et al., "Actions Of Vitamin $D_3$ Analogs on Human Prostate Cancer Cell Lines: Comparison with 1,25–Dihydroxyvitamin $D_3$," *Endocrinology*, (1995) 136:20–26.

Skowronski et al., "Vitamin D and Prostate Cancer: 1,25 Dihydroxyvitamin $D_3$ Receptors and Actions in Human Prostate Cancer Cell Lines," *Endocrinology*, (1993) 132:1952–1960.

Slapak, C. et al., "Treatment of Acute Myeloid Leukemia in the Elderly with Low–Dose Cytarabine, Hydroxyurea, and Calcitriol," *Amer. J. Hematology*, (1992) 41:178–183.

Sommerfeldt et al., "Metabolism of Orally Administered [$^3$H]Ergocalciferol and [$^3$H]Cholecalciferol by Dairy Calves," *J. Nutr.*, (1983) 11:2595–2600.

Song, X.D. et al., "Bryostatin–1 and 1α,25–Dihydroxyvitamin $D_3$ Synergistically Stimulate the Differentiation of NB4 Acute Promyelocytic Leukemia Cells," *Leukemia*, (1999) 13:275–281.

Sorensen, O.H, et al., "Treatment of Senile Osteoporosis with 1α-Hydroxyvitamin $D_3$," *Clin. Endocrinol.*, (1977) 7:169S–175S.

Studzinski, G. et al., "Potentiation by 1–α,25– Dihydroxyvitamin $D_3$ of Cytotoxicity to HL–60 Cells Produced by Cytarabine and Hydroxyurea," *J. National Cancer Inst.*, (Apr. 1986) 76:4:641–648.

Strugnell et al., "Metabolism of a Cyclopropane–Ring–Containing Analog of 1α–Hydroxyvitamin $D_3$ in a Hepatocyte Cell Model," *Biochem. Pharm.*, (1990) 40:333–341.

Strugnell et al., "1 α,24(S)–Dihydroxyvitamin $D_2$: a biologically active product of 1 α–hydroxyvitamin $D_2$ made in the human hepatoma, Hcp3B," *Biochem. J.*, (1995) 310:233–241.

Suzuki, Y. el al., "The Enhancement of the Chemotherapeutic Effects on Human Prostate Cancer Cell—The Combination with the Growth Factor Interaction Inhibitor (Suramin)," *Acta Urologica* (1993) 12:1215–1220, (Abstract).

Swami, S. et al. "1α,25–Dihydroxyvitamin $D_3$ Down–Regulates Estrogen Receptor Abundance and Suppresses Estrogen Actions in MCF–7 Human Breast Cancer Cells," *Clinical Cancer Research*, (Aug. 2000) 6:3371–3379.

Tachibana, Y. (Nisshin Flour Milling Co.), "Preparation of 1Beta–Hydroxyvitamin $D_2$ and $D_3$," *CHEMICAL ABSTRACTS*, (1990) 113:1:6688 Col. 2 Abstract No. 6683y.

Tanaka, Y. et al., *Endocrinology* (1973) 92:417–422.

Torres, R. et al., Etoposide Stimulates 1,25–Dihydroxyvitamin $D_3$ Differentiation Activity, Hormone Binding and Hormone Receptor Expression in HL–60 Human Promyelocytic Cells, *Molecular and Cellular Biochemistry*, (2000)208:157–162.

Tsuji, M. et al., "Synthesis of 22,23–Dihydro–1α,25–Dihydroxyvitamin $D_2$ and its 24R–Epimer, New Vitamin $D_2$ Derivatives," *Bull. Chem. Soc. Jpn.*, (1990) 63:8:2233–2238.

Wang, Q. et al., "1,25–Dihydroxyvitamin $D_3$ and All–*trans*–Retinoic Acid Sensitize Breast Cancer Cells to Chemotherapy–induced Cell Death," *Cancer Research*, (Apr. 2000) 60:2040–2048.

Wang, X. et al., "Inhibition of p38 MAP Kinase Activity Up–Regulates Multiple MAP Kinase Pathways and Potentiates 1,25–Dihydroxyvitamin $D_3$–Induced Differentiation of Human Leukemia HL6O Cells," *Experimantal Cell Research*, (2000) 258:425–437.

Wientroub, S. et al. "The Dichotomy in the Effects of 1,25 Dihydroxy Vitamin $D_3$ and 24, 25 Dihydroxy Vitamin $D_3$ on Bone Gamma–Carboxyglutamic Acid–Containing Protein in Serum and Bone in Vitamin D–Deficient Rats," *Calcif, Tissue Int.*, (1987) 40:166–172.

Windaus, A. et al., "Uber das Krystallisierte Vitamin $D_4$," *Z. Physiol. Chem.*, (1937) 247:185–188.

Yu, W. et al., "Enhancement of 1,25– Dihydroxyvitamin $D_3$–Mediated Antitumor Activity with Dexamethasone," *J. National Cancer Inst.*, (Jan. 1998) 90:2:134–141.

Zerwekh et al., "Short–Term 1,25–Dihydroxyvitamin $D_3$ Administration Raises Serum Osteocalcin in Patients with Postmenopausal Osteoporosis," *J. Clin. Endocrinol. Metabol*, (1985) 60:615–617.

1α–Hydraxyergocalciferol, Vitamin D Workshop, *Product Information* (1994).

10th Vitamin D Workshop–Letter to Participants, *Solvay Duphar* (1997).

1α–Hydroxyergocalciferol—Certificate of Analysis, *Solvay Pharmaceuticals* (2002).

Vitamin $D_2$, 1α–Hydroxy—Product Data Sheet, *Calbiochem* (1998).

Moriarty et al., "Synthesis and Stereochemical Studies on 1α and 1β–hydroxy Vitamin $D_2$"—Eighth Workshop on Vitamin D, Paris France (1991).

Vitamin $D_2$, 1α–Hydroxy—Safety Data Sheet, *Calbiochem* (2000) 1–3.

* cited by examiner

STABILIZED HYDROXYVITAMIN D

CROSS-REFERENCE TO RELATED APPLICATIONS

This application is a continuation-in-part under 35 U.S.C. §111 from International Application No. PCT/US01/22729 filed Jul. 18, 2001 which designated the United States and which claims priority to U.S. provisional patent application No. 60/219,068 filed Jul. 18, 2000.

STATEMENT REGARDING FEDERALLY SPONSORED RESEARCH OR DEVELOPMENT

Not Applicable

This invention relates a stabilized hydroxyvitamin D ("SHVD") which is particularly well suited for pharmaceutical formulations.

Vitamin D compounds having a hydroxy group at the 1α and 24 positions have had considerable attention in recent years because of their strong vitamin D activity. These activated vitamin D compounds are, however, also known as being chemically unstable, particularly under exposure of light and in the presence of oxygen, and as having poor storage stability at higher temperatures. The compounding of activated vitamin D into a pharmaceutical formulation exacerbates these stability problems.

Despite recognition and study of various aspects of the problem as well as prior art attempts to stabilize pharmaceutical compositions of activated vitamin D, the prior art has produced very little in the way of an active vitamin D form that has a specific chemical and physical profile which provides for a stabilized compound useful for pharmaceutical formulations. It has now been found that a stabilized 1α-hydroxyvitamin D and 24-hydroxyvitamin D with heretofore unknown technical properties are surprisingly stable compared to known forms of activated vitamin D.

The present invention relates to a stabilized hydroxy vitamin D form with superior technical properties and superior stability (SHVD). SHVD is particularly well adapted for use in pharmaceutical compositions or formulations. Accordingly, the present invention will now be described in detail with respect to such endeavors; however, those skilled in the art will appreciate that such a description of the invention is meant to be exemplary only and should not be viewed as limitative on the full scope thereof.

In the following description of the method of the invention, process steps are carried out at room temperature and atmospheric pressure unless otherwise specified.

As used herein, the term "vitamin D" is intended to include vitamins $D_2$, $D_3$ and $D_4$ and related analogs. The term "1α-hydroxyvitamin D" refers to a vitamin D compound or analog that has a substituted hydroxy group in at least the carbon-1α position of the A ring of the compound. Those compounds that are substituted only with a hydroxy in the 1α-position, e.g., 1α-hydroxyvitamin $D_2$ and 1α-hydroxyvitamin $D_3$, are pro-drugs as they undergo further hydroxylation to form metabolically active vitamin D compounds. Those compounds that are hydroxylated in the 24 or 25 position as well as the 1α position are typically metabolically active vitamin D compounds, i.e., 1α, 24-dihydroxyvitamin $D_2$ and 1α, 25-dihydroxyvitamin $D_3$. The term "24-hydroxyvitamin D" refers to a vitamin D compound or analog that has a substituted hydroxy group in at least the 24 carbon of the compound. The term "active vitamin D" or "activated vitamin D" references to a vitamin D compound that is hydroxylated in at least the 1α, 24 or 25 position. As used herein, the term "stabilized hydroxyvitamin D" or "SHVD" is meant to include, but is not limited to, any stabilized 1α-hydroxyvitamin D and any stabilized 24-hydroxyvitamin D. The term "SHVD" is not meant to include certain commercially available vitamin D compounds, i.e., excludes 1α-hydroxyvitamin $D_3$, 1α,25-dihydroxyvitamin $D_3$, 1,24-dihydroxyvitamin $D_3$, 22-oxa-1, 25-dihydroxyvitamin $D_3$ (OCT), paricalcitol (a 19-norvitamin $D_2$) and calcipotriol. The term "non-SHVD" refers to 1α-hydroxyvitamin D and 24 hydroxyvitamin D compounds that do not meet the purity profile and other characteristics described herein for SHVD.

SHVD of the present invention is crystalline, substantially solvent free, storage stable and well suited for modem therapy formulations. Studies have demonstrated that SHVD with the technical properties found in the present invention is surprisingly stable, particularly its reduced rate of conversion to the corresponding previtamin form on heat challenge or elevated temperature. SHVD in accordance with the present invention shows virtually no degradation after 6 years storage at −70° C. This corresponds to excellent storage stability when formulated in a pharmaceutical dosage form, e.g., a soft gelatin capsule. The SHVD of the present invention does not require low oxygen or inert atmosphere for storage as has been advanced by some prior art stabilized formulations.

SHVD of the present invention is also characterized in that it has an ultraviolet spectrum peak maximum ($\lambda_{max}$) at about 265 nm with a molar extinction coefficient, $\Sigma_{265\ nm}$ of 17490 and a minimum ($\lambda_{min}$) at about 227 nm, and has a specific purity profile. SHVD has a purity equal to or greater than 98% weight-base (i.e., at least 98%) by high performance liquid chromatography (HPLC), has residual solvents of 0.5% or less, has total impurities of 1.5% or less, and has no single impurity greater than 0.5% by HPLC. The impurities include cis-1α-OH-$D_4$ and cis-1β-OH-$D_2$. While not wanting to be bound by any particular theory, it is believed that the remarkable stability of SHVD is related to its being substantially solvent free and substantially free of impurities.

The SHVD in accordance with the present invention is further characterized by a substantially reduced rate of conversion to the corresponding previtamin upon heat challenge when compared to the same non-SHVD. This stability of SHVD with respect to conversion to the corresponding previtamin D is especially surprising. A 1α-hydroxyvitamin D compound is in thermal equilibrium with its previtamin form, i.e., they are thermal isomers of each other.

By way of example, the equilibrium for 1α-OH-$D_2$ is illustrated below.

1a-OH-D$_2$    1a-OH-pre D$_2$

The 1α-hydroxyprevitamin D$_2$ has a characteristic ultraviolet spectrum peak maximum ($\lambda_{max}$) at 259 nm. Storage of the 1α-hydroxyvitamin D form in solution or at elevated temperatures produces the 1α-hydroxy previtamin D form. The isomers are in equilibrium with each other even at room temperature. Increased temperature shifts the equilibrium to the formation of the previtamin.

The SHVD of the present invention shows reduced rate of conversion to 1α-hydroxy previtamin D compared to corresponding non-SHVD compounds under the same conditions, e.g., a heat challenge. The heat challenge is suitably an elevated temperature held in air for a sustained period, which period may be up to 10 days. The elevated temperature is suitably about 60° C. Upon such heat challenge the SHVD of the present invention has a lower rate of conversion compared to that for a non-SHVD compound under the same conditions.

Figure 1:
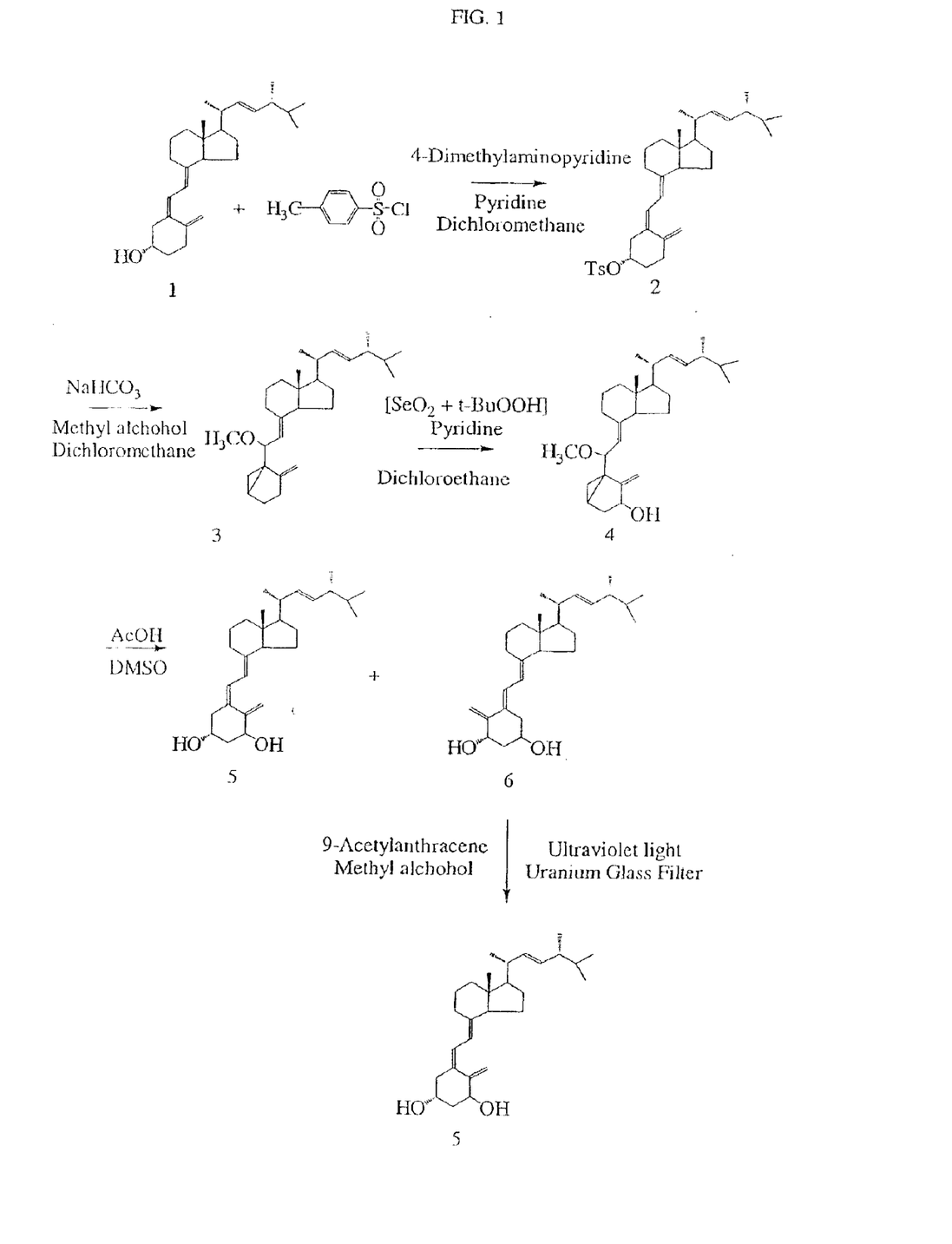
FIG. 1 is an exemplary reaction scheme for the synthesis of 1α-hydroxyvitamin $D_2$.

1α-hydroxyvitamin D compounds may be prepared by any of the known methods of synthesis. It has been found that certain synthetic pathways provide a compound that, upon purification, may have the superior technical properties of the SHVD of the present invention. An exemplary synthetic scheme is shown in FIG. 1 illustrating the synthesis of 1α-hydroxyvitamin D$_2$ (also known as doxercalciferol). Generally, the synthesis includes conversion of a starting material vitamin D (i.e., the compound that is to be hydroxylated in the 1α-position) to the cyclovitamin form, hydroxylation of the cyclovitamin in the 1α-position, reconversion of the hydroxylated cyclovitamin to the cis and trans forms of the vitamin, and conversion of the trans form to the cis form. The hydroxy group in the 3-position is protected, suitably by conversion to a tosylate as a first step in the synthesis.

By way of example, as shown is FIG. 1, vitamin D$_2$ (or ergocalciferol) is the starting material. Vitamin D$_2$ is first tosylated in the 3-position to form vitamin D$_2$ 3-tosylate. The tosylate is then converted to the cyclovitamin that is then 1α-hydroxylated. The hydroxylated cyclovitamin is then converted to cis and trans 1α-hydroxyvitamin D$_2$. The trans isomer is irradiated with ultraviolet light to convert to the cis isomer, i.e., 1α-hydroxyvitamin D$_2$.

The resulting product is purified by column chromatography. The column-purified 1α-hydroxyvitamin D$_2$ is then recrystallized from an organic solvent, e.g., methyl formate. The recrystallized crystals are then vacuum oven dried to a residual solvent content of <0.5% to provide SHVD. The SHVD in accordance with the present invention is particularly satisfactory when successive (generally at least two) recrystallizations are performed. Suitable solvents, in addition to methyl formate, include ethyl formate, ethyl acetate, acetone, methylethylketone, hexane, 2-propanol-hexane, pentane, heptane, diethyl ether, diisopropyl ether, methanol, ethanol acetonitrile, and combinations thereof.

24-hydroxyvitamin D compounds may also be prepared by any of the known methods of synthesis (see, e.g., U.S. Pat. No. 6,242,434, incorporated herein by reference). Generally, the synthesis includes conversion of a starting material vitamin D (i.e., the compound that is to be hydroxylated in the 24-position) to the cyclovitamin form, hydroxylation of the cyclovitamin in the 24-position, reconversion of the hydroxylated cyclovitamin to the cis and trans forms of the vitamin, and conversion of the trans form to the cis form. The hydroxy group in the 3-position is protected, suitably by conversion to a tosylate as a first step in the synthesis.

The SHVD of the present invention is suitably used in pharmaceutical formulations, such as for oral use, e.g., soft gelatin capsules, solutions, tablets. The concentration of active ingredient in convenient unit dosage form is 0.5 µg to 25 µg, with a weekly dose of between 1 µg and 100 µg/week. In a soft gelatin formulation, the capsule fill suitably contains SHVD of the present invention which is dissolved in a pharmaceutically acceptable oil, e.g., fractionated coconut oil, and includes an antioxidant which may be, for example, butylated hydroxyanisole (BHA), butylated hydroxytoluene (BHT) or vitamin E. The capsule shell suitably contains gelatin, glycerin, titanium dioxide and coloring agent. The fill is typically about 58–59% by weight of the whole capsule.

The present invention is further explained by the following examples, which should not be construed by way of limiting the scope of the present invention.

In the examples, UV spectra were taken on a Shimadzu UV 160V, IR spectra on a Analect DS-20, and NMR on a SEOL NMR spectrometer operating at 400 MH$_3$ or like instruments known in the art.

Preparation of Stabilized 1α-hydroxyvitamin D$_2$ (SHVD$_2$)

EXAMPLE 1

Preparation of 1α-hydroxyvitamin D$_2$ Crude Drug Substance (1) Preparation of Ergocalciferol Tosylate (2)

To 100 g of ergocalciferol (vitamin D$_2$) was added 3.1 g of 4-dimethylaminopyridine, 100 mL anhydrous pyridine, and 340 mL anhydrous dichloromethane. The flask contents were stirred until the internal reaction temperature was ≦5° C. Then, 122.6 g of p-toluenesulfonyl chloride was added, and the mixture stirred until all the solids were dissolved. The reaction was allowed to proceed with slow stirring under argon. After 32 hours, the completion of the reaction was monitored by TLC (silica gel plates; ethyl acetate in hexanes; 20% phosphomolybdic acid in ethanol).

Over a period of approximately 20 minutes, the reaction mixture was dripped into a chilled beaker containing saturated sodium bicarbonate. The reaction mixture was rinsed into a separatory funnel with 900 mL isopropyl ether. The mixture was extracted with isopropyl ether by shaking, and the organic and aqueous layers separated. The isopropyl ether extracts were washed with dilute hydrochloric acid, saturated sodium bicarbonate, and saturated sodium chloride. The combined isopropyl ether extracts were dried over 250 g of anhydrous magnesium sulfate and filtered. The isopropyl ether extracts were combined and concentrated in vacuo. The crude tosylate was suitable for use in the solvolysis below.

(2) Preparation of 6(R)-methoxy-3,5-cyclovitamin $D_2$(3)

To a stirred mixture of 1950 mL of dry methyl alcohol and 500 g of sodium bicarbonate was added the ergocalciferol tosylate from Step 1 dissolved and rinsed in 250 mL dichloromethane. The stirred mixture was refluxed under an argon atmosphere for 18–22 hours with an internal temperature of about 56° C. After about 20 hours, the extent of reaction was monitored by TLC (silica gel; solvents 20% phosphomolybdic acid in ethanol).

The reaction mixture was cooled to 25–30° C., and the sodium bicarbonate was removed by filtration. The reaction flask, filtered sodium bicarbonate and filtration flask were rinsed with 1000 mL of isopropyl ether. The organic filtrate was concentrated in vacuo, maintaining the temperature of the bath at 50° C. The semi-solid residue was diluted with isopropyl ether. This isopropyl ether solution was washed three times with water and once with saturated sodium chloride, and then dried over magnesium sulfate. The magnesium sulfate was removed by filtration and rinsed with isopropyl ether. The combined organic filtrate and the isopropyl ether rinse of the filtration flask were concentrated in vacuo for 4–18 hours to yield the 6(R)-methoxycyclovitamin.

(3) Preparation of 1α-hydroxy-6(R)-methoxy-3,5-cyclovitamin $D_2$(4)

To a stirred suspension of 12.3 g of freshly ground selenium dioxide in 1500 mL of 1,2-dichloroethane was added 81 mL of anhydrous t-butyl hydroperoxide (5–6 M in decane). After stirring under positive argon atmosphere for 3–4 hours at ambient temperature, 18 mL of pyridine was added. The 6(R)-methoxy-3,5-cyclovitamin $D_2$ from Step 2, dissolved in 1,2-dichloroethane, was added dropwise into the chilled reaction flask followed by a rinse of 1,2-dichloroethane. The reaction continued with stirring at an internal temperature of <5° C., and the reaction progress was monitored at 15-minute intervals by TLC. The reaction was considered complete when the starting 6(R)-methoxy-3,5-cyclovitamin $D_2$ was either no longer visible or did not appear to change between two consecutive monitoring thin layer chromatograms.

The reaction was quenched with 10% sodium hydroxide. The aqueous and organic layers were separated, and the aqueous layer was extracted with isopropyl ether. This isopropyl ether extract was added to the organic layer from the reaction mixture. The combined extracts were dried with anhydrous magnesium sulfate and filtered. The flask and residual magnesium sulfate were rinsed with isopropyl ether, and the combined isopropyl ether extracts and isopropyl ether rinse of the filtration flask were concentrated in vacuo.

The product was dissolved in 500 mL of 5% ethyl acetate in hexanes, purified on a silica gel (60/230–400 Mesh) in a column (75 mm I.D.), and eluted with approximately 4000 mL 5% ethyl acetate in hexanes, followed by 8000 mL 20% ethyl acetate in hexanes under positive argon pressure. Fractions of approximately 200 mL each were collected during the elution. The fractions were analyzed by silica gel TLC. The fractions containing the 1α-hydroxy-6(R)-methoxy-3,5-cyclovitamin $D_2$ were identified, combined, and concentrated in vacuo.

(4) Preparation of cis- and trans-1α-hydroxyvitamin $D_2$(5 and 6)

A stirred solution of the 1α-hydroxy-6(R)-methoxy-3,5-cyclovitamin $D_2$ from Step 3 in 120 mL of dimethyl sulfoxide and 130 mL of glacial acetic acid was heated to about 60° C. and stirred at this temperature under an argon atmosphere for 60 minutes. The reaction was monitored periodically by silica gel TLC for the consumption of the reactant 1α-hydroxy-6(R)-methoxy-3,5-cyclovitamin $D_2$. Upon completion, the reaction was cooled to 20–25° C. The reaction was quenched by pouring the mixture and an isopropyl ether rinse into saturated sodium bicarbonate and water held at a temperature ≦110° C. Isopropyl ether was added and the mixture was stirred. This mixture was then rinsed into a separatory funnel with 950 mL isopropyl ether and extracted by shaking. The aqueous and organic layers were separated. The aqueous layer was extracted with isopropyl ether. The organic layer from the reaction mixture was combined with this isopropyl ether extract and washed with saturated sodium bicarbonate three times, water three times, and saturated sodium chloride once. The organic extracts were dried over magnesium sulfate, filtered, and the cake magnesium sulfate and filtration flask were rinsed with isopropyl ether. The combined isopropyl ether filtrates were concentrated in vacuo, maintaining the temperature of the bath at about 35° C. Residual solvent was removed from the remaining residue by vacuum.

The product, dissolved in 350 mL dichloromethane, was purified on silica gel (60/230–400 mesh) in a column (75 mm I.D.) eluted with 40% ethyl acetate in hexanes under argon. Fractions of approximately 125 mL were collected. The fractions were analyzed by silica gel TLC eluted with 40% ethyl acetate in hexanes. The fractions containing cis- and trans-1α-OH-$D_2$ were identified, combined, and concentrated in vacuo.

(5) Preparation of cis-1α-hydroxyvitamin $D_2$(5)

The cis- and trans-1α-OH-$D_2$ mixture from Step 4 and 1.1 g of 9-acetylanthracene were dissolved in 2000 mL methyl alcohol and transferred with methyl alcohol rinses totaling 2000 mL to a photolysis chamber and diluted with additional methyl alcohol to a total of 13.7 L. The photolysis was run to completion, approximately 2–6 hours. The product solution and 400 mL methyl alcohol rinse were concentrated in vacuo, maintaining the temperature of the bath around 35° C.

The residual solvent was removed under high vacuum. The product, dissolved in dichloromethane, was purified on silica gel (60/230–400 mesh) in a column (75 mm I.D.) eluted with 40% ethyl acetate in hexanes and ethyl acetate under argon pressure. Fractions (125 mL) were collected with 40% ethyl acetate in hexanes elution, then fractions (200 mL) were collected with 100% ethyl acetate elution. The fractions were analyzed by silica gel TLC eluted with 40% ethyl acetate in hexanes. The fractions containing the cis-1α-OH-$D_2$ were identified, combined, and concentrated in vacuo, The residual solvent was removed under high vacuum. A typical yield for this step was 15–30 g (15–30% overall yield from the starting material, ergocalciferol).

EXAMPLE 2

Purification of Crude Drug Substance to Yield $SHVD_2$

The column-purified cis-1α-hydroxyvitamin $D_2$ (crude drug substance) was successively recrystallized from methyl formate.

For each recrystallization, the column-purified crude drug substance (usually 15–30 g) was resuspended in 3500 mL methyl formate in a round bottom flask. This flask was attached to a rotary evaporator with a chilled condenser and slowly rotated in a water bath at 40° C. until the solids dissolve. The solution was concentrated in the rotary evaporator, maintained at 40° C. until crystals began to form. When crystals were observed, the flask was placed in a –20° C. freezer to cool for 48–72 hours.

After the crystals obtained from the recrystallization had air dried for 5–10 minutes, the crystals were milled to a powder, and then, transferred to a crystallization dish. The dish with crystals was placed in a vacuum oven set at about 55° C. for 72–120 hours. The amount of drug substance obtained ($SHVD_2$) was usually 5–10 g, which represents a yield of 5–10% of the starting material, ergocalciferol.

Figure 2A:
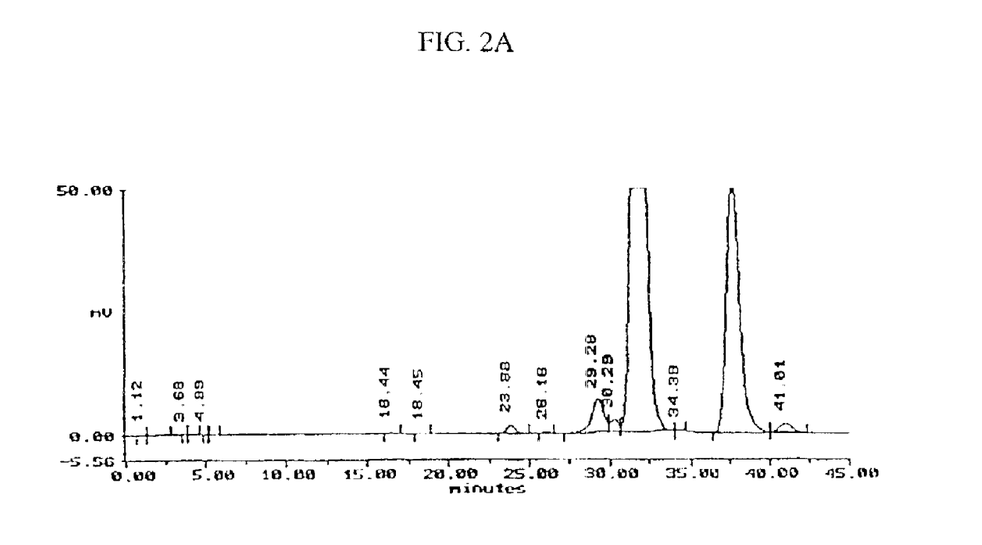
FIGS. 2A and 2B are HPLC chromatograms showing the preparation of SHVD in accordance with the present invention.
Figure 2B:
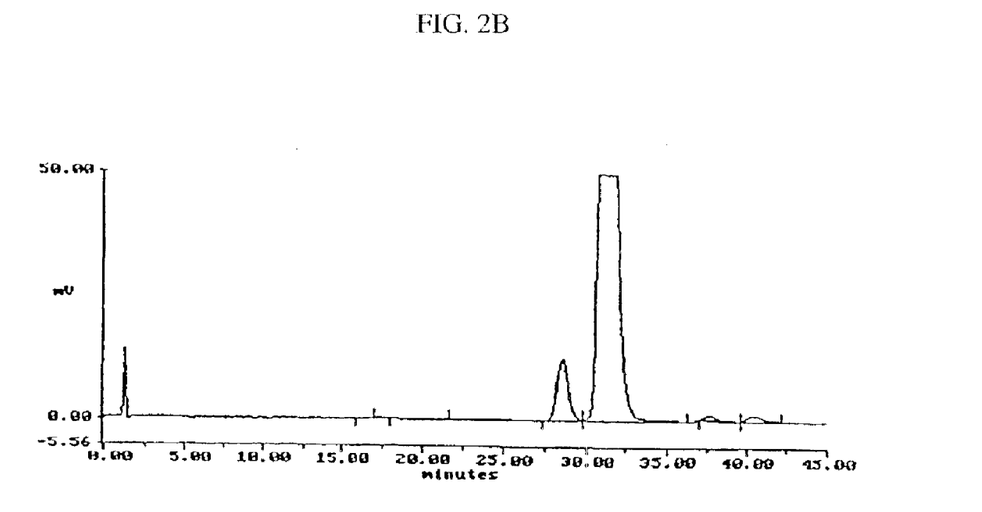

Evidence that the purification procedure improved the purity of the crude drug substance was demonstrated by the HPLC chromatogram in FIG. 2. The first chromatogram (A) was obtained with column-purified crude drug substance. Chromatogram (B) shows the final product. As shown in FIG. 2, the levels of the impurities with retention times of approximately 37.7 and 41 minutes were reduced by recrystallization.

EXAMPLE 3

Determination of Residual Solvents of $SHVD_2$

A method for quantitating residual solvents with toluene was used. The target analytes included methanol, methyl formate, methylene chloride, hexane, diisopropyl either, 1,1-dichloroethane and ethyl acetate.

A gas chromatographic method was used with helium as the carrier gas, split injections/run, and run in single ion mode (SIM mode). It required a 60 m×0.25 mm ID, DB-624 capillary column with a film thickness of 1.4 μm, a split/splitless injector, a gas chromatograph capable of ramping from 50° C. to 250° C., and a mass selective detector. The chromatograph was set to detect ions 31, 32, 43, 45, 49, 60, 61, 62, 84, 86 and 87 at a dwell time of 25 ms per ion.

An external calibration was used, consisting of a blank, matrix blank and a 4-point curve. A curve was prepared at concentration of 1 μg/g, 10 μg/g and 50 μg/g. A 10 mg sample of cis-1α-OH-$D_2$ was prepared in toluene. Results from the samples were calculated using the linear curve generated above. The lower limit for all analytes was 100 μg/g. The results indicated that the amount of residual solvents in the cis-1α-OH-$D_2$ ($SHVD_2$) was ≦0.5%

EXAMPLE 4

Storage Stability Testing of $SHVD_2$

The stability of samples from four lots of $SHVD_2$ was examined at 6-month intervals during long-term storage at –70° C. All lots were stored in the container-closure system selected as packaging for the drug substance. Stability was assessed by examining samples for changes in (1) weight percent 1α-OH-$D_2$ content, (2) percent related substances content, and (3) impurity profile, using HPLC. In addition, all lots were examined for changes in UV spectrum by UV spectrophotometry.

Results of this study showed no significant differences in mean weight % 1α-OH-$D_2$ content between baseline and 6 or 12 months. The weight % 1α-OH-$D_2$ content for all lots examined was >98.0% at all time points. Impurity profile chromatography demonstrated no new peaks at 6 or 12 months relative to baseline. The percent related substances remained <2.0%.

EXAMPLE 5

Preparation of $SHVD_2$ Soft Gelatin Capsule Fill

BHA was added to fractionated coconut oil (FCO), heated and stirred until the BHA was completely dissolved. This solution was then cooled. $SHVD_2$ was accurately weighed into a suitable container, dehydrated alcohol was added, and the solution was stirred until the $SHVD_2$ was dissolved. FCO was weighed into a stainless steel mixing tank. The BHA/FCO solution was added to the FCO while stirring. Then $SHVD_2$/dehydrated alcohol solution was added and the solution was stirred until uniform. The vessel containing the $SHVD_2$/dehydrated alcohol solution was rinsed with dehydrated alcohol and the rinses were added to the FCO/$SHVD_2$/dehydrated alcohol mix. The mixing tank containing this mix was sealed, a vacuum was applied, and the contents were mixed (deaerated). The resulting solution was transferred through filters to receivers and blanketed with nitrogen.

EXAMPLE 6

Stability Testing: SHVD2 v. Non-$SHVD_2$

Approximately 1 mg of $SHVD_2$ or non-stabilized 1α-hydroxyvitamin $D_2$ (non-$SHVD_2$) is placed in each of 9 (12×75 mm) test tubes. The test tubes are placed in an oven at about 60° C. One test tube of each of the two vitamin $D_2$ preparations is removed at 0, 3, 6, 9, 12, 18, 24, 36 and 48 hours of incubation. The contents in each test tube are dissolved in ethanol to produce a 1 mg/mL solution. Each solution (10 μL) is analyzed by the following HPCL conditions: a YMC Pack C8 column (4.6×250 mm, 5 μm) with a mobile phase of acetonitrile: methanol: water (60:20:20) at a flow rate of 1.0 mL/min. The rate of appearance of the peak migrating with a relative retention time of approximately 0.9 compared with the 1α-hydroxyvitamin $D_2$ peak is greater with the non-$SHVD_2$ than with $SHVD_2$.

EXAMPLE 7

Stability Testing: $SHVD_2$ v. Commercially Available 1α-OH-$D_2$

Approximately 1 mg of $SHVD_2$ or commercial 1α-hydroxyvitamin $D_2$ is placed in each of 2 (12×75 mm) test tubes. One test tube from each of the two preparations is placed in an oven at about 60° C. For analysis, the contents in each test tube are dissolved in ethanol to produce a 1 mg/mL solution. Each solution (10 μL) is analyzed by the following HPLC conditions: a YMC Pack C8 column (4.6× 250 mm, 5 μm) with a mobile phase of acetonitrile: methanol: water (60:20:20) at a flow rate of 1.0 mL/min. The rate of appearance of the peak migrating with a relative retention time of approximately 0.9 compared with the 1α-hydroxyvitamin $D_2$ peak is greater with the commercial 1α-hydroxyvitamin $D_2$ than with $SHVD_2$.

EXAMPLE 8

Stability Testing of $SHVD_2$ v. Non-$SHVD_2$

Approximately 1 mg of stabilized 1α-hydroxyvitamin $D_2$ (doxercalciferol) ($SHVD_2$) was placed in each of two test tubes (12×75 mm). One sample was placed in a dessicator containing an atmosphere of ethanol vapors to increase the residual solvent content of the material to form non-stabilized doxercalciferol (non-$SHVD_2$). The material in the dessicator was heated at 60° C. for 48 hours. The other sample was not subjected to the ethanol atmosphere, thereby retaining its stabilized form, but was heated at 60° C. for 48 hours. The contents in each test tube were dissolved in ethanol to produce a 1 mg/mL solution. Each solution (10 μL) was analyzed by the following HPLC conditions: a YMC Pack C8 column (4.6×250 mm, 5 μm) with a mobile phase of acetonitrile: methanol: water (60:20:20) at a flow rate of 1.0 mL/min. The rate of appearance of the peak migrating with a relative retention time of approximately 0.9 compared with the doxercalciferol peak is greater with the non-$SHVD_2$ material than with $SHVD_2$.

EXAMPLE 9

Stability Testing: 1α,24(S)-dihydroxyvitamin $D_2$ Containing >0.5% Residual Solvents (a Non-$SHVD_2$)

Approximately 1 mg of 1α,24(S)-dihydroxyvitamin $D_2$ containing >0.5% residual solvents (non-SHVD) was placed in a capped vial and heated at 60° C. for 48 hours. The contents of the vial were dissolved in ethanol to produce a 1 mg/mL solution. The solution (10 μL) was analyzed by the following HPLC conditions: a YMC Pack Pro C18 column (4.6×150 mm, 5 μm) with a mobile phase of acetonitrile: water (50:50) at a flow rate of 1.0 mL/min. After heating the non-SHVD, a compound with a relative retention time of approximately 0.85 compared with standard 1α,24(S)-dihydroxyvitamin $D_2$ was observed.

EXAMPLE 10

Purification of 24-Hydroxyvitamin $D_2$ to Yield Stabilized 24-Hydroxyvitamin $D_2$ 24-hydroxyvitamin $D_2$ is synthesized according to generally known procedures such as those set forth in U.S. Pat. No. 6,242,434 (incorporated herein by reference).

The 24-hydroxyvitamin $D_2$ is successively recrystallized from methyl formate.

For each recrystallization, the 24-hydroxyvitamin $D_2$ (usually 15–30 g) is resuspended in 3500 mL methyl formate in a round bottom flask. This flask is attached to a rotary evaporator with a chilled condenser and slowly rotated in a water bath at 40° C. until the solids dissolve. The solution is concentrated in the rotary evaporator, maintained at 40° C. until crystals begin to form. When crystals are observed, the flask is placed in a −20° C. freezer to cool for 48–72 hours.

After the crystals obtained from the recrystallization have air dried for 5–10 minutes, the crystals are milled to a powder, and then, transferred to a crystallization dish. The dish with crystals is placed in a vacuum oven set at about 55° C. for 72–120 hours.

EXAMPLE 11

Storage Stability Testing of Stabilized 24-Hydroxyvitamin $D_2$

The stability of samples from four lots of stabilized 24-Hydroxyvitamin $D_2$ is examined at 6-month intervals during long-term storage at −70° C. All lots are stored in the container-closure system selected as packaging for the drug substance. Stability is assessed by examining samples for changes in (1) weight percent 24-OH-$D_2$ content, (2) percent related substances content, and (3) impurity profile, using HPLC. In addition, all lots are examined for changes in UV spectrum by UV spectrophotometry.

No significant differences are found in mean weight % 24-OH-$D_2$ content between baseline and 6 or 12 months. The weight % 24-OH-$D_2$ content for all lots examined is >98.0% at all time points. Impurity profile chromatography demonstrates no new peaks at 6 or 12 months relative to baseline. The percent related substances remains <2.0%.

In summary, the present invention provides SHVD, a stabilized hydroxyvitamin D form with superior technical properties and superior stability. The novel form of the present invention is crystalline, substantially solvent free, stable and well suited for modern therapy formulations.

While the present invention has now been described and exemplified with some specificity, those skilled in the art will appreciate the various modifications, including variations, additions, and omissions, which may be made in what has been described. Accordingly, it is intended that these modifications also be encompassed by the present invention and that the scope of the present invention be limited solely by the broadest interpretation that lawfully can be accorded the appended claims.

We claim:

1. A stabilized 1α-hydroxyvitamin $D_2$ characterized by a purity equal to or greater than 98% by a weight-based HPLC assay, residual solvents of 0.5% or less, a total impurity of 1.5% or less, and no single impurity of greater than 0.5%.

2. A pharmaceutical composition comprising an active component which is the stabilized 1α-hydroxyvitamin $D_2$ of claim 1.

3. The composition of claim 2, which is a soft gelatin, capsule.

4. The composition of claim 2 which is a solution.

5. The composition of claim 4, wherein the solution is contained in a vial.

6. The composition of claim 2, in unit dosage form, having a content of active component of 0.5 μg–25 μg.

7. A composition which comprises a solution of an effective amount of the stabilized 1α-hydroxyvitamin $D_2$ of claim 1 in an oil, the solution contained in a soft gelatin capsule.

8. The composition of claim 7 wherein the oil comprises fractionated coconut oil.

9. The composition of claim 7, which further comprises an antioxidant.

10. The composition of claim 9, wherein the antioxidant is selected from the group consisting of butylated hydroxyanisole (BHA), butylated hydroxytoluene (BHT) or vitamin E.

11. The composition of claim 10, wherein the antioxidant is butylated hydroxyanisole (BHA).

12. The composition of claim 10, wherein the antioxidant is butylated hydroxytoluene (BHT).

13. The composition of claim 10, wherein the antioxidant is vitamin E.

14. A composition which comprises a solid pharmaceutical preparation of an effective amount of the stabilized 1α-hydroxyvitamin $D_2$ of claim 1, wherein the solid pharmaceutical preparation is in the form of a tablet, a capsule, a granule or a powder.

15. The composition of claim 14, wherein the pharmaceutical preparation is in the form of a tablet.

16. The composition of claim 14, wherein the pharmaceutical preparation is in the form of a capsule.

17. The composition of claim 14, wherein the pharmaceutical preparation is in the form of a granule.

18. The composition of claim 14, wherein the pharmaceutical preparation is in the form of a powder.

19. A pharmaceutical composition consisting essentially of a stabilized 1-αhydroxyvitamin $D_2$ according to claim 1 and a pharmaceutically acceptable carrier.

* * * * *